Figure 1:
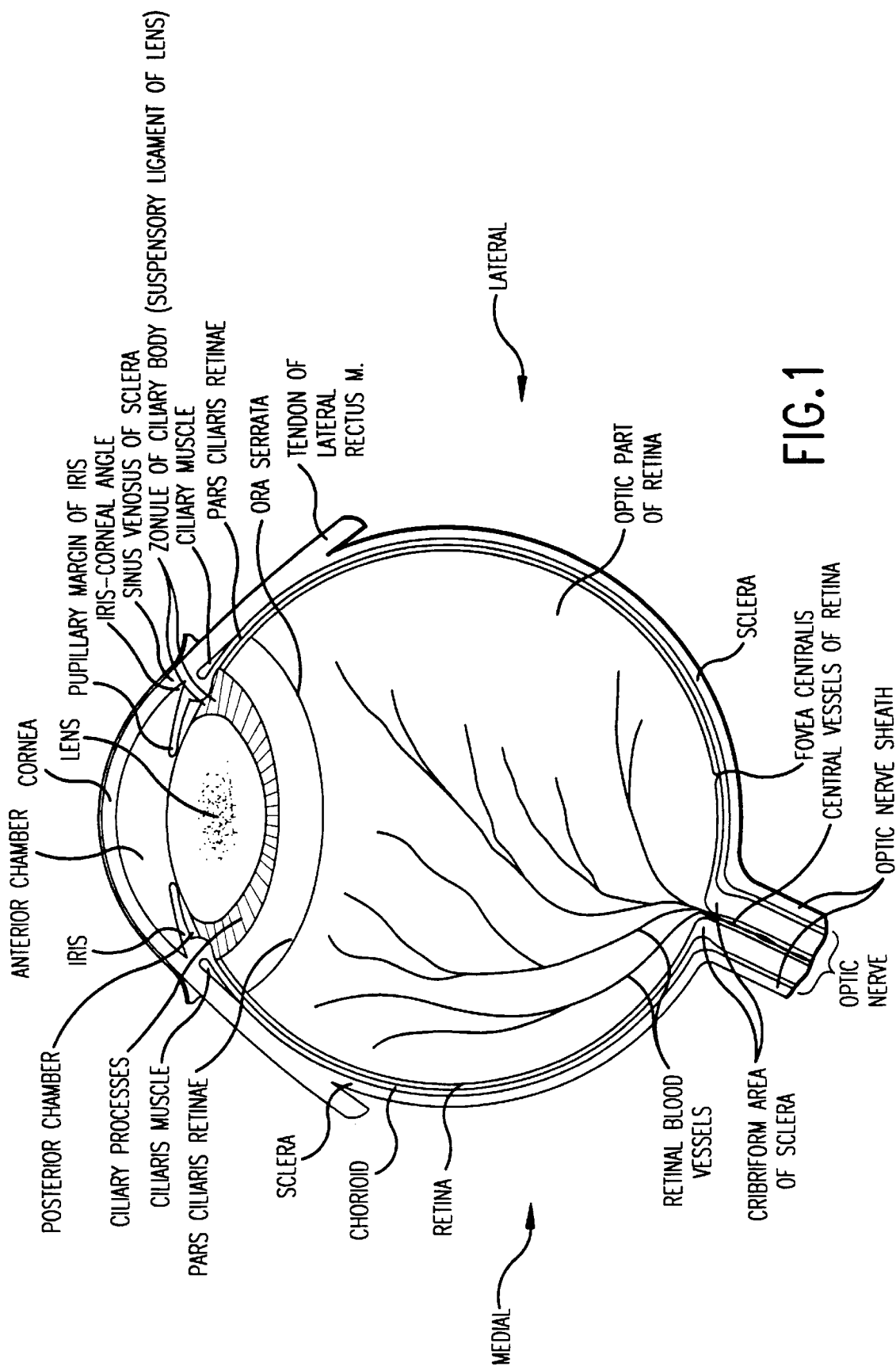

United States Patent [19]
Galin et al.

[11] Patent Number: 5,965,152
[45] Date of Patent: Oct. 12, 1999

[54] CONTROLLED RELEASE OF MIOTIC AND MYDRIATIC DRUGS IN THE ANTERIOR CHAMBER

[76] Inventors: Miles A. Galin, 180 E. End Ave., New York, N.Y. 10128; Joseph C. Salamone, 2202 NW. 62nd Dr., Boca Raton, Fla. 33496; Stanley C. Israel, 675 West St., Carlisle, Mass. 01741

[21] Appl. No.: 08/815,896

[22] Filed: Mar. 12, 1997

Related U.S. Application Data

[62] Division of application No. 08/423,703, Apr. 18, 1995, Pat. No. 5,612,027.

[51] Int. Cl.$^6$ .................................. A61F 2/00; A61K 9/14
[52] U.S. Cl. ........................... 424/426; 424/427; 424/489
[58] Field of Search .................................. 424/400, 78.04, 424/427

[56] References Cited

U.S. PATENT DOCUMENTS

| | | | |
|---|---|---|---|
| 4,141,973 | 2/1979 | Balazs | 424/180 |
| 4,303,637 | 12/1981 | Shell et al. | 424/14 |
| 4,305,927 | 12/1981 | Theeuwes et al. | 424/15 |
| 4,668,506 | 5/1987 | Bawa | 424/429 |
| 4,713,244 | 12/1987 | Bawa et al. | 424/429 |
| 4,863,457 | 9/1989 | Lee | 604/891.1 |
| 4,911,920 | 3/1990 | Jani et al. | 424/78 |
| 4,931,279 | 6/1990 | Bawa et al. | 424/427 |
| 5,007,913 | 4/1991 | Dulebohn et al. | 606/107 |
| 5,093,126 | 3/1992 | Jani et al. | 424/428 |
| 5,098,443 | 3/1992 | Parel et al. | 623/4 |
| 5,318,780 | 6/1994 | Viegas et al. | 424/427 |
| 5,612,027 | 3/1997 | Galin et al. | |

OTHER PUBLICATIONS

Joshi, Journal of Ocular Pharmacology, vol. 10(1):29–45, 1994.
Couvreur et al., Derwent Drug File (DRUGU), 95–13495, 1995.
Joshi, DRUGU, 94–29564, 1994.
Schoenwald, 1993, "Pharmacokinetics in Ocular Drug Delivery" (chapter 10), Biopharmaceuticals of Ocular Drug Delivery, CRC Press, Inc., Boca Raton, FL.
Hayakawa et al. 1983, Macromolecules 16:1642.
Couvreur, et al., Eur. J. Pharm. Biopharm. 41(1):2–13, 1995.
Joshi, J. Ocul. Pharmacol. 10(1):29–45,1994.

Primary Examiner—Thurman K. Page
Assistant Examiner—Sharon Howard
Attorney, Agent, or Firm—Baker & Botts, L.L.P.

[57] ABSTRACT

The present invention relates to compositions which maintain the structural integrity of the anterior chamber of the eye during ophthalmologic surgery, thereby protecting the tissues that form and line the anterior segment from potential damage and simultaneously providing sustained delivery of a miotic or mydriatic agent. The present invention provides for compositions which comprise a viscoelastic polymer, wherein sustained release of a miotic or mydriatic agent is mediated by ionic interactions, as well as for compositions wherein sustained release of a miotic or mydriatic agent is mediated by microcapsules or copolymer micelles.

5 Claims, 2 Drawing Sheets

CONTROLLED RELEASE OF MIOTIC AND MYDRIATIC DRUGS IN THE ANTERIOR CHAMBER

CROSS-REFERENCED TO RELATED APPLICATIONS

This is a divisional of application Ser. No. 08/423,703, filed on Apr. 18, 1995 U.S. Pat. No. 5,612,027.

1. INTRODUCTION

The present invention relates to compositions, comprising a viscoelastic polymer and a miotic or mydriatic agent, which maintain the structural integrity of the anterior chamber of the eye during ophthalmological surgery, thereby protecting the tissues that form and line the anterior segment from potential damage and simultaneously providing sustained delivery of a miotic or mydriatic agent. The present invention also provides for compositions wherein sustained release of a miotic or mydriatic agent is mediated by microcapsules or copolymer micelles.

2. BACKGROUND OF THE INVENTION

Maintaining the integrity of the anatomic components of the eye facilitates the delicate manipulations, performed within small areas, of ophthalmological surgery.

One component which may be controlled is the anterior chamber of the eye. As shown in FIG. 1, the anterior chamber is located between the cornea and the iris. Just posterior to the iris is the lens, which is interposed between the anterior chamber and the larger vitreous chamber, filled with vitreous humor. Maintaining the structural integrity of the anterior chamber minimizes the risk that the endothelium and/or the iris will be damaged during surgery. The introduction of viscoelastic materials, such as sodium hyaluronate, chondroitin sulfate, hydroxypropyl methylcellulose, and methylcellulose, into the anterior chamber prevents the chamber from collapsing during surgery.

Another component that may be controlled is pupil size. During cataract surgery, it is desirable that the pupil is dilated, so that access to the lens is simplified and the insertion of a posterior chamber implant is facilitated. A variety of mydriatic drugs, such as atropine (a cholinergic blocker), phenylephrine (an adrenergic stimulator), and prostaglandin inhibitors have been used in this regard, and have hitherto predominantly been administered via external application.

Conversely, in refractive implants and secondary aphakic implants, a smaller ("miotic") pupil is desirable, in order to reduce iris trauma, avoid anterior synechias, prevent iris tucking, and facilitate appropriate positioning of the implant. Externally applied pilocarpine and carbachol (cholinergic stimulators), and physostigmine, demecarium bromide, echothiophate iodide, and isofluorphate (cholinesterase inhibitors) have been used for this purpose.

During surgery, however, and in the open eye, the efficacy of topical medication is reduced. Dilution and runoff preclude a continued high dose of effective medication. Even the direct introduction of miotic agents such as acetylcholine chloride or carbachol do not provide long term effects and often require frequent repeated administration into the open eye.

Previous attempts to achieve long-term maintenance of effective drug levels have employed sustained drug delivery technology, using systemic or transdermal administration, or the positioning of a bioerodible drug delivery device external to the eye. Such methods have been used primarily to control intraocular pressure in glaucoma patients. However, prior to the present invention, no method has been devised which combines sustained mydriatic or miotic drug delivery with maintenance of the structural integrity of the anterior chamber.

3. SUMMARY OF THE INVENTION

The present invention relates to compositions which may be used to maintain the structural integrity of the anterior chamber of the eye and to provide sustained release of a miotic or mydriatic agent. In various embodiments of the invention, compositions of the invention comprise a viscoelastic polymer, wherein sustained release of a miotic or mydriatic agent is mediated by ionic interactions. In further embodiments of the invention, sustained release of a miotic or mydriatic agent is mediated by microcapsules or copolymer micelles. In particular embodiments, the compositions of the invention may be used to provide both rapid release of miotic or mydriatic agent as well as slower, sustained release.

4. DESCRIPTION OF THE FIGURE

FIG. 1. Clemente, 1978, in "Anatomy", Lea and Fibiger, Philadelphia, FIG. 501.

Figure 2:
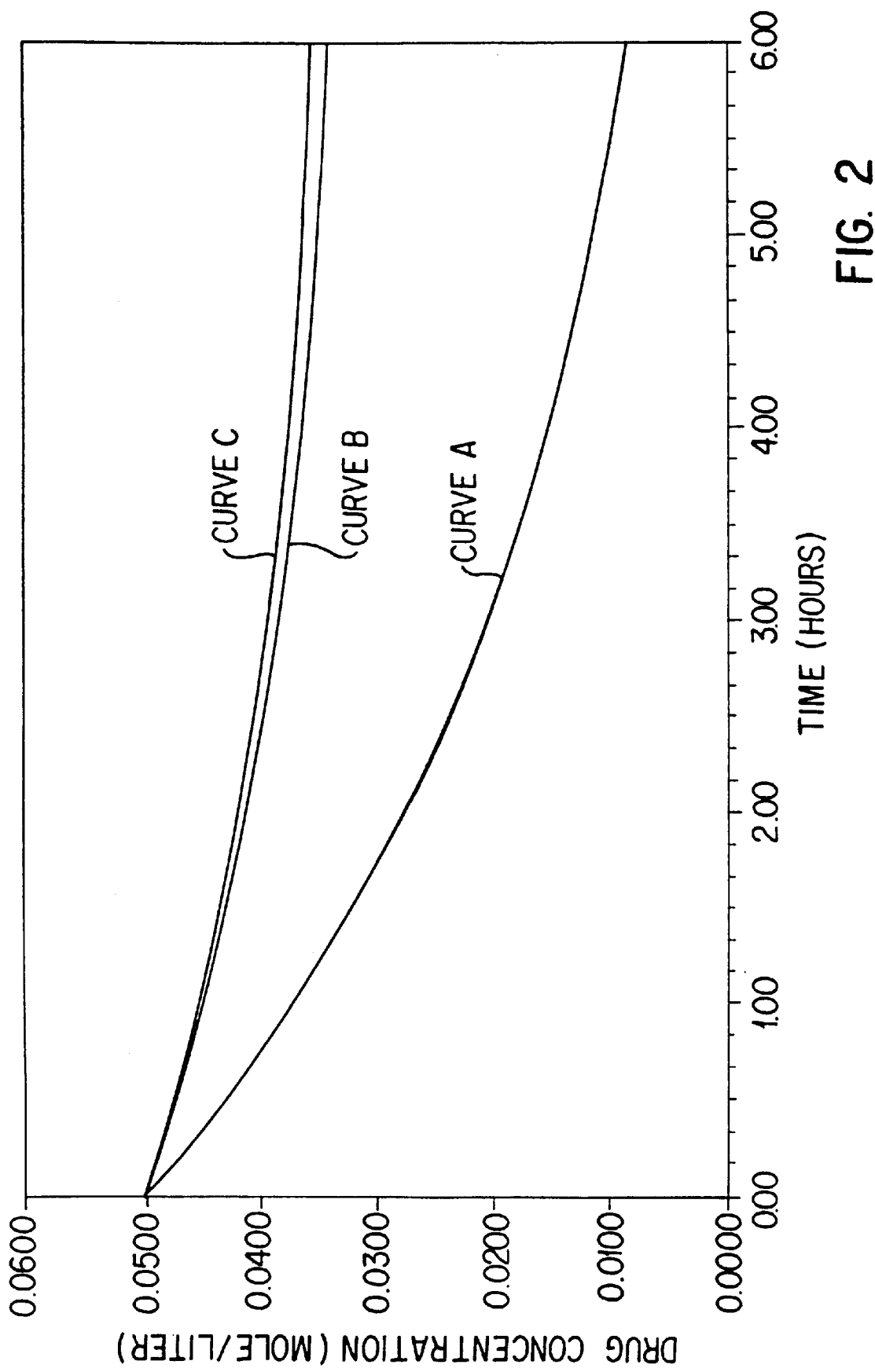

FIG. 2. Dilution effect of miotic or mydriatic agents in the anterior chamber of the eye caused by the normal turnover rate of aqueous humor, in the presence or absence of viscoelastic polymer-drug complex. Curve A represents unbound drug=0.0500 moles/liter in physiological saline; Curve B represents unbound drug=0.025 moles/liter plus viscoelastic polymer-drug complex=0.0500 equivalents/liter in physiological saline; and Curve C represents viscoelastic polymer-drug complex=0.100 equivalents/liter in physiological saline.

5. DETAILED DESCRIPTION OF THE INVENTION

For clarity of presentation, and not by way of limitation, the detailed description of the invention is divided into the following sections:

(1) viscoelastic polymers;
(2) miotic agents;
(3) mydriatic agents;
(4) compositions of the invention; and
(5) methods for using the compositions of the invention.

5.1. VISCOELASTIC POLYMERS

The present invention provides for compositions comprising viscoelastic polymers, including but not limited to the anionic viscoelastic polymers hyaluronic acid (hyaluronate), chondroitin sulfate, dermatan sulfate, carboxymethylcellulose, heparin sulfate, keratan sulfate, carboxymethylhydroxypropylcellulose, carboxymethylhydroxethylcellulose, cellulose sulfate, cellulose phosphate, carboxymethylguar, carboxymethylhydroxypropylguar, carboxymethylhydroxyethylguar, xanthan gum, carrageenan, anionic polysaccharides, anionic proteins and polypeptides, anionic polyacrylamide, anionic poly-N-vinylpyrrollidone, anionic polydimethyl acrylamide, polymers and copolymers of 2-acrylamido-2-methyl-propanesulfonic acid, acrylic acid and methacrylic acid. The foregoing compounds, in their non-ionized forms, may function as acidic polymers; in their ionized forms, the compounds may function as polymeric anions.

The viscoelastic polymers of the invention range in molecular weight from 50,000 to 8,000,000 daltons, depending on the polymer of choice. For example, an average molecular weight of from 1,000,000 to 5,000,000 daltons is commonly used for sodium hyaluronate, whereas an average molecular weight of greater than 80,000 daltons is normally used for hydroxypropylmethylcellulose. The concentration of viscoelastic polymer may vary from 1 mg/ml to 60 mg/ml, and preferably from 5 mg/ml to 30 mg/ml. The viscosity of the viscoelastic polymer may vary from 1000 centistokes to 60,000 centistokes, and preferably from 2,500 centistokes to 5,500 centistokes for hydroxypropylmethylcellulose and from 20,000 centistokes to 40,000 centistokes for sodium hyaluronate. Such viscosities not only enable the introduction of the polymer into the eye by injection or extrusion, but also are viscous enough to remain within the anterior chamber (that is to say, will not run off easily), maintain its structural integrity, and permit easy withdrawal. Furthermore, the viscoelastic polymers of the invention are water soluble and can be eluted with time.

5.2. MIOTIC AGENTS

The present invention provides for compositions comprising miotic agents including, but not limited to, pilocarpine, isopilocarpine, pilocarpine hydrochloride, pilocarpine nitrate, isopilocarpine hydrochloride, isopilocarpine nitrate, carbachol, physostigmine, physostigmine sulfate, physostigmine sulfite, demecarium bromide, ecothiophate iodide and acetylcholine chloride. Preferred agents are members of the pilocarpine and isopilocarpine family of compounds.

The miotic agents of the invention may be utilized in either neutral or charged, cationic form, depending on the nature of the sustained drug delivery to be provided by the composition. Of the foregoing list, agents that are considered basic include: pilocarpine, isopilocarpine, and physostigmine; agents that are considered hydrophobic include: pilocarpine, isopilocarpine, and physostigmine; and agents that are considered cationic include demecarium bromide, ecothiophate iodide, pilocarpine hydrochloride, pilocarpine nitrate, isopilocarpine hydrochloride, isopilocarpine nitrate, carbachol, physostigmine sulfate, acetylcholine chloride and physostigmine sulfite.

5.3. MYDRIATIC AGENTS

The present invention provides for compositions comprising mydriatic agents including, but not limited to, atropine, atropine sulfate, atropine hydrochloride, atropine methylbromide, atropine methylnitrate, atropine hyperduric, atropine N-oxide, phenylephrine, phenylephrine hydrochloride, hydroxyamphetamine, hydroxyamphetamine hydrobromide, hydroxyamphetamine hydrochloride, hydroxyamphetamine iodide, cyclopentolate, cyclopentolate hydrochloride, homatropine, homatropine hydrobromide, homatropine hydrochloride, homatropine methylbromide, scopolamine, scopolamine hydrobromide, scopolamine hydrochloride, scopolamine methylbromide, scopolamine methylnitrate, scopolamine N-oxide, tropicamide, tropicamide hydrobromide, and tropicamide hydrochloride. Preferred agents are members of the atropine family and phenylephrine family of compounds.

The mydriatic agents of the invention may be utilized in either neutral or charged, cationic form, depending on the nature of the sustained drug delivery to be provided by the composition. Of the foregoing list, agents that are considered basic include: atropine, phenylephrine, hydroxyamphetamine, cyclopentolate, homatropine, scopolamine, and tropicamide; agents that are hydrophobic include atropine, phenylephrine, hydroxyamphetamine, cyclopentolate, homatropine, scopolamine, and tropicamide; and agents that are considered cationic include atropine sulfate, atropine hydrochloride, atropine methylbromide, atropine methylnitrate, atropine hyperduric, atropine N-oxide, phenylephrine hydrochloride, hydroxyamphetamine iodide, hydroxyamphetamine iodide, hydroxyamphetamine hydrobromide, cyclopentolate hydrochloride, homatropine hydrobromide, homatropine hydrochloride, homatropine methylbromide, scopolamine hydrobromide, scopolamine hydrochloride, scopolamine methylbromide, scopolamine methylnitrate, scopolamine N-oxide, tropicamide, and tropicamide hydrobromide.

5.4. COMPOSITIONS OF THE INVENTION

The present invention provides for compositions which provide sustained release of miotic or mydriatic agents, as described above, in which release of the agent is mediated by (1) ionic (including acid-base) interactions; (2) microcapsules; or (3) copolymer micelles. The compositions also provide a means for maintaining the structural integrity of the anterior chamber of the eye.

In a first set of nonlimiting embodiments, the present invention provides for compositions in which the sustained release of miotic or mydriatic agent is achieved through ionic interactions between the agent and a viscoelastic polymer. In particular embodiments, a composition may comprise an anionic viscoelastic polymer and a cationic miotic or mydriatic agent, in which case the cationic agent of the composition, when placed in the eye, may be released by displacement with endogenous sodium or potassium ions, or other naturally occurring cations. In one specific, nonlimiting embodiment, the anionic viscoelastic polymer acid may be sodium hyaluronate, and the cationic agent may be the mydriatic agent atropine sulfate, where, in the preparation of the composition, sodium sulfate (and bisulfate) are removed by using an excess of the atropine sulfate in the presence of a lesser amount of sodium hyaluronate followed by dialysis. This process may be repeated several times to prepare a high purity of atropine hyaluronate. In another specific, nonlimiting embodiment, the anionic viscoelastic polymer may be chondroitin sulfate and the cationic agent may be the miotic agent pilocarpine, which may be combined by interacting sodium chondroitin sulfate with pilocarpine hydrochloride. In yet another specific, nonlimiting embodiment, an ion exchange interaction between sodium hyaluronate and phenylephrine hydrochloride can be effected, yielding phenylephrine hyaluronate.

In a second, related set of nonlimiting embodiments, the present invention provides for compositions in which the sustained release of miotic or mydriatic agent is achieved through ionic acid-base interactions between the agent and a viscoelastic polymer. In particular embodiments, a composition may comprise an acidic viscoelastic polymer and a basic miotic or mydriatic agent, in which case the composition, when placed in the approximately pH neutral environment of the eye, will provide a relatively slow release of the miotic or mydriatic agent by ionic displacement of the drug from existing cations. In one specific, nonlimiting embodiment, the acidic viscoelastic polymer acid may be hyaluronic acid, and the basic agent may be the mydriatic agent atropine. When these two compounds are combined in the composition, the polymeric salt atropine hyaluronate may be formed. In another specific, nonlimiting embodiment, hyaluronic acid may be interacted with the basic miotic drug pilocarpine in water at a temperature range of 5 to 50° C. (wherein the pilocarpine becomes protonated by the polyacid and is rendered a salt of the viscoelastic polymer), followed by dialysis or ultrafiltration to remove unreacted pilocarpine. The resulting pilocarpine hyaluronate composition may then, alternatively, either be sterilized and adjusted to the appropriate pH and osmolality for use (for example, and not by way of limitation, where the pH range is between about 6.8 and 7.8, preferably between 7.2 and 7.4, and the osmolality is 285±55 mOsm/kg and preferably between 290 and 320 mOsm/kg), or may be recovered by drying in vacuo or by lyophilization. In yet another specific, nonlimiting embodiment of the invention, hyaluronic acid may be interacted with the mydriatic agent phenylephrine in aqueous solution, using an excess of phenylephrine, followed by dialysis, yielding phenylephrine hyaluronate.

In a nonlimiting example relating to the sustained release of a miotic or mydriatic agent from the anterior chamber of the eye, FIG. 2 depicts three representative conditions using an aqueous humor volume of 310 microliters and an aqueous humor turnover rate of 1.5 microliters per minute (Schoenwald, 1993, "Pharmacokinetics in Ocular Drug Delivery" (Chapter 10) in *Biopharmaceuticals of Ocular Drua Delivery*, CRC Press, Inc., Boca Raton, Fla.). Units for unbound drug are given in moles per liter, and units for viscoelastic polymers are given in units of equivalents per liter, which would describe any viscoelastic polymer with any miotic or mydriatic drug.

In FIG. 2, curve A represents unbound drug, wherefor the initial concentration of 0.0500 moles/liter is diminished to 0.0084 moles/liter after 6 hours of dilution in the eye, caused by the turnover rate of aqueous humor.

Curve B of FIG. 2 represents a combination of unbound drug (no viscoelastic polymer present) and ion-complexed (bound) drug-viscoelastic polymer. In this curve, the viscoelastic polymer-drug complex has a predicted cooperative binding constant of $5 \times 10^{-2}$ (Hayakawa et al., 1983, Macromolecules 16:1642). This value was determined for carboxymethylcellulose (as a model anionic viscoelastic polymer) with a hydrophilic cation of dodecyltrimethylammonium ion. From curve B it may be seen that, with an initial concentration of unbound drug of 0.0500 moles per liter, at 6 hours of aqueous humor turnover, 0.0340 moles per liter of medicament remains in the anterior chamber. This final concentration is more than 4-fold greater than the final concentration of unbound drug observed after 6 hours.

Curve C of FIG. 2 represents ion-complexed (bound) drug-viscoelastic polymer, wherein the initial concentration of 0.100 equivalents per liter (producing an equilibrium initial concentration of 0.500 moles per liter of unbound drug) is reduced to 0.0354 moles per liter after 6 hours of duration in the eye, caused by the turnover of aqueous humor. This final concentration is more than 4 times greater than the final concentration of unbound drug, and slightly greater than that of Curve B. In this curve, the viscoelastic polymer-drug complex has a predicted cooperative binding constant of $5 \times 10^{-2}$ (Hayakawa et al., 1983, Macromolecules 16:1642).

Thus, from FIG. 2 it may be seen that two conditions of ion-complexed miotic or mydriatic drug/polymer complex clearly demonstrate the effect of sustained release of drug with time, as compared to unbound drug, in the anterior chamber of the eye.

In a third set of nonlimiting embodiments, the present invention provides for compositions which comprise microcapsules that are soluble or swellable in aqueous media and preferably biodegradable, which themselves comprise miotic or mydriatic agent, wherein the agent may be eluted with time as the microcapsule slowly dissolves, disintegrates, or swells. Typically, such microcapsules may desirably be smaller than the wavelength of light in order to prevent light scattering and impaired vision. In this procedure the agent of choice is incorporated into the microcapsule during formation of the microcapsule. Since the viscosity of microcapsules is typically low, a viscoelastic polymer may be added to maintain the anterior chamber.

Soluble microcapsules may be derived from inherently biodegradable polymers, such as poly-DL-lactide or poly-DL-lactide-co-glycolide, which, in dry form, may be made into microcapsules containing an appropriate agent (Clarke et al., 1994, Polymer Preprints 35(2):73). Alternatively, soluble microcapsules may be derived from pH sensitive polymers, where a change in pH can cause expansion of the microcapsule, leading to a sustained release drug delivery system. An example of such a pH-sensitive polymer is poly(L)-lysine-alt-terephthalic acid, which, at pH values greater than 6, expands (Makino et al., 1994, Polymer Preprints 35: 54). Biodegradable microcapsules containing miotic or mydriatic agent may be prepared using polymers, such as polylactide or polylactide-co-glycolide, that decompose after a period of time.

In a fourth set of nonlimiting embodiments, the present invention provides for compositions which comprise soluble copolymer micelles comprising a miotic or mydriatic agent, wherein the micelles comprise a hydrophilic and a hydrophobic portion, and the agent (in its uncharged form) is absorbed into the hydrophobic portion of the copolymer micelle (Arca et al., 1994, Polymer Preprints 35: 71). At equilibrium, a hydrophobic drug, such as phenylephrine, may be expected to reside both inside and outside the copolymer micelle. When the preparation is placed in the anterior chamber of the eye, as the exterior agent is removed, the interior agent may be slowly released. Such copolymer micelles may preferably be hydrophilic-hydrophobic or hydrophilic-hydrophobic-hydrophilic in character. Preferably, the hydrophilic blocks are derived from ethylene oxide and the hydrophobic blocks from propylene oxide (ethylene oxide-propylene oxide-ethylene oxide block copolymers are sold under the trade names of Pluronic or Ploxamer). Compositions comprising copolymer micelles may be mixed with a viscoelastic polymer, such as hydroxypropylmethylcellulose, in order to maintain the structural integrity of the anterior chamber.

The present invention further provides for compositions comprising a plurality of miotic agents, or a plurality of mydriatic agents.

The amount of miotic or mydriatic agent present in the composition may be that amount which produces the desired therapeutic effect; that is to say, the desired pupil size for the desired period of time. Such amounts will vary between agents, but may readily be determined using the dose-response relationships known to the skilled artisan. The concentration of mitoic or mydriatic agent may vary from 0.001 mg/ml to 20 mg/ml, and preferably from 0.025 mg/ml to 10 mg/ml. As one specific, nonlimiting example, where the miotic drug is acetylcholine chloride, a polymer/drug complex formulation may be prepared using a solution of acetylcholine chloride with acetylcholine hyaluronate, where the acetylcholine concentration may be 10 mg/ml and the osmolality may be adjusted to 305 mosm/kg by mannitol. As another specific, nonlimiting example, where the miotic agent is pilocarpine hydrochloride, a polymer/drug complex formulation may be prepared using a solution of pilocarpine hydrochloride with pilocarpine hyaluronate, where the pilocarpine concentration may be 1 mg/ml and the osmolality may be adjusted to 305 mosm/kg by mannitol. As yet another specific, nonlimiting example, using the mydriatic drug atropine sulfate, a solution of atropine hyaluronate containing atropine sulfate may be prepared where the atropine concentration may be 0.3 mg/ml and the osmolality may be adjusted to 305 mosm/kg by mannitol. In each of the foregoing examples in this paragraph, the cationic drug may be mixed with the polymer-drug complex in sterile water and the osmolality may then be adjusted using the neutral agent mannitol.

Because it is important, during ophthalmologic surgery, to maintain the osmolality of the anterior chamber of the eye, the compositions of the invention preferably exhibit an osmolality such that their introduction into the eye may not detrimentally alter the osmolality of the anterior chamber. The osmolality of the natural contents of the anterior chamber has been reported to be 301–305 mosm/kg (Geigy Scientific Tables, Volume 1, Ed. C. Lentner, Eighth Edition, 1981, Basle, Switzerland). The osmolality of viscoelastic polymer drug ion complex could be maintained by excess drug in its salt form (for example, a 3.0% solution of phenylephrine chloride is isotonic in comparison to a 0.9 weight percent NaCl solution), or by a solution of, or in combination with, a neutral agent, such as glycerine (where a 2.6 weight percent solution is isotonic relative to a 0.9 weight percent NaCl solution) or mannitol (where a 5.07% solution is isotonic relative to a 0.9 weight percent NaCl solution). If traditional isotonic solutions are used, which may contain sodium ions, potassium ions, calcium ions, etc., such ions may prematurely displace the ion-complexed drug, releasing it into solution, and an excess of the cationic drug may be required to be added in order to readjust the polymer-drug equilibrium. In preferred embodiments of the invention, the osmolality of the compositions may be between about 280 and 340 mosm/kg, and preferably between about 280–340 mOsm/kg.

In order to maintain the structural integrity of the anterior chamber of the eye, the compositions of the invention must be sufficiently viscous such as to prevent the chamber from collapsing during surgical manipulation. The compositions should also, however, be sufficiently fluid to permit their introduction into the anterior chamber by injection or extrusion, as well as their removal (for example, by irrigation) at the conclusion of the surgical procedure. Accordingly, the viscosity of a composition according to the invention is between 1,000 and 60,000 centistokes and preferably between 2,500 and 40,000 centistokes. Where viscoelastic polymers are used, the concentrations of viscoelastic polymer are preferably between about 10 mg/ml and 30 mg/ml in aqueous (preferably isotonic) solution.

5.5. METHODS OF USING COMPOSITIONS OF THE INVENTION

The compositions of the invention are particularly useful when employed during a variety of ophthalmological surgical procedures, such as procedures desirably performed while the pupil is dilated, including intracapsular and extracapsular surgery and fistulizing procedures, and procedures desirably performed while the pupil is miotic, including anterior segment surgery, such as surgical separation of vitreo/corneal adhesions, separation of iris/corneal adhesions, and the placement of phakic refractive implants and secondary aphakic implants.

For example, and not by way of limitation, compositions comprising a mydriatic agent, according to the invention, may be used in standard extracapsular cataract surgery carried out under topical or retrobulbar anesthesia. It should be noted that retrobulbar anesthesia tends to make the iris somewhat more sensitive to dilating or constricting drops (Starling's Law). The mydriatic composition of the invention may then be injected into the anterior chamber before and/or after an appropriate capsulotomy. Irrigation, aspiration, expression, or phacoemulsification of the cataract may then be performed. The implant may then be inserted, and residual mydriatic viscous material may be irrigated from the eye. In such procedures, the composition of the invention may aid the extraction of the lens and implant placement.

In another nonlimiting example, miotic compositions according to the invention may be used in standard myopic refractive implant placement procedures. After a paracentesis is carried out, the miotic composition may be injected into the anterior chamber. Then, an entrance incision may be made, the implant may be positioned, the wound may be sutured, and the viscous miotic composition may be irrigated from the eye.

The use of compositions of the invention offer a number of advantages. First, the present invention provides for a composition which may simultaneously provide both mechanical and pharmaceutical activities useful in ophthalmological surgery. Second, the compositions of the invention may be used to satisfy a long-felt need for a means for providing sustained release of miotic or mydriatic agents during surgery. Third, the compositions of the invention may prevent or reduce a rise in intraocular pressure which may be associated with the use of a viscoelastic solution which does not comprise a miotic agent. Fourth, the use of compositions of the invention may be used to prevent posterior or anterior synechias by keeping the pupil dilated during the immediate post-operative phase.

Moreover, during conventional surgery, with loss of the chamber and hypotony there is loss of iris tone and function. Since the viscous compositions of the invention maintain the chamber and some degree of intraocular pressure, and are in contact with the iris for a prolonged period of time, a reservoir effect is established so that chamber maintenance, enhanced iris tone and response and drug delivery are concurrently achieved. Further, particularly when miosis is desired, the long term effect of miotics may blunt the pressure elevatory potential of the viscoelastic.

Various publications are cited herein, which are hereby incorporated by reference in their entireties.

What is claimed is:

1. A composition for intracameral use in ophthalmologic surgery comprising biodegradable microcapsules that maintain the structural integrity of the eye which comprise a viscoelastic polymer and an agent selected from the group consisting of miotic agents and mydriatic agents.

2. The composition according to claim 1 wherein the microcapsules are constructed of polylactide.

3. The composition according to claim 1 where the microcapsules are constructed of copoly (lactideglycolide).

4. A method of maintaining the structural integrity of the anterior chamber of the eye during surgery while concurrently maintaining the desired pupil size comprising administering the composition of claim 1.

5. A method of maintaining the structural integrity of the posterior chamber of the eye during surgery while concurrently maintaining the desired pupil size comprising administering the composition of claim 1.

* * * * *

UNITED STATES PATENT AND TRADEMARK OFFICE
CERTIFICATE OF CORRECTION

PATENT NO. : 5,965,152
DATED : October 12, 1999
INVENTOR(S) : Galin et al.

It is certified that error appears in the above-identified patent and that said Letters Patent is hereby corrected as shown below:

Column 2,
Line 62, "vinylpyrrollidone" should read -- vinylpyrrolidone --.

Column 3,
Line 26, "physostic" should read -- physostig --.

Column 6,
Line 51, "mitoic" should read -- miotic --.
Line 59, "mosm/kg" should read -- mOsm/kg --.
Line 64, "mosm/kg" should read -- mOsm/kg --.

Column 7,
Line 2, "mosm/kg" should read -- mOsm/kg --.
Lines 13 and 29, "mosm/kg" should read -- mOsm/kg --.

Signed and Sealed this

Fourth Day of June, 2002

Attest:

JAMES E. ROGAN
Attesting Officer     Director of the United States Patent and Trademark Office